United States Patent
Frid

(10) Patent No.: US 7,588,597 B2
(45) Date of Patent: Sep. 15, 2009

(54) THREE-DIMENSIONAL BRAIDED STRUCTURE STENT

(75) Inventor: Noureddine Frid, Beersel (BE)

(73) Assignees: F.R.I.D. R&D Benelux SPRL, Mons (BE); Cardiatis SA, Mons (BE)

( * ) Notice: Subject to any disclaimer, the term of this patent is extended or adjusted under 35 U.S.C. 154(b) by 306 days.

(21) Appl. No.: 10/450,315

(22) PCT Filed: Dec. 12, 2001

(86) PCT No.: PCT/BE01/00210

§ 371 (c)(1), (2), (4) Date: Nov. 21, 2003

(87) PCT Pub. No.: WO02/47579

PCT Pub. Date: Jun. 20, 2002

(65) Prior Publication Data

US 2004/0215332 A1    Oct. 28, 2004

(30) Foreign Application Priority Data

Dec. 12, 2000 (BE) .................................. 2000/0783
Mar. 13, 2001 (EP) .................................. 01870042

(51) Int. Cl.
*A61F 2/44* (2006.01)
(52) U.S. Cl. ...................... 623/1.5; 623/1.51; 623/1.15; 623/1.39; 623/1.44
(58) Field of Classification Search ........................ None
See application file for complete search history.

(56) References Cited

U.S. PATENT DOCUMENTS

| 5,061,275 | A | * | 10/1991 | Wallsten et al. ............ 623/1.22 |
| 5,718,159 | A | * | 2/1998 | Thompson ..................... 87/33 |
| 5,957,974 | A | | 9/1999 | Thompson et al. |
| 6,004,346 | A | | 12/1999 | Wolff et al. |

FOREIGN PATENT DOCUMENTS

| EP | 0 804 902 A2 | 11/1997 |
| EP | 0 938 878 A2 | 9/1999 |
| GB | 1205743 | 9/1970 |
| WO | WO 99/55256 | 11/1999 |

OTHER PUBLICATIONS

EPO International Search Report, Jun. 12, 2003.

* cited by examiner

*Primary Examiner*—Corrine M McDermott
*Assistant Examiner*—Christopher D Prone
(74) *Attorney, Agent, or Firm*—Christie, Parker & Hale, LLP

(57) ABSTRACT

A modular luminal endoprosthesis consisting of a framework, generally called a stent, and more particularly an endoprosthesis for blood vessels. The framework (6) of this stent comprises a plurality of interconnected layers (8, 10, 12), each of these layers (8, 10, 12) being formed by two plies of metal wires (14), which are respectively dextrogyratory and laevogyratory, and which are interlaced and form a lattice, a plurality of wires (14) of a given layer (8, 10, 12) being integrated in the lattice of at least one of the adjacent layers (8, 10, 12).

10 Claims, 2 Drawing Sheets

THREE-DIMENSIONAL BRAIDED STRUCTURE STENT

CROSS-REFERENCE TO RELATED APPLICATIONS

This application claims priority of PCT International Application No. PCT/BE01/00210, filed 12 Dec. 2001; which claimed foreign priority benefits of Belgium Patent Application No. BE-2000/0783, filed 12 Dec. 2000, and European Patent Application No. EP 01870042.7, filed 13 Mar. 2001. The disclosures of each of the foregoing applications are incorporated herein by reference.

BACKGROUND OF THE INVENTION

The invention relates to the luminal endoprostheses formed principally of a framework, without textile covering, generally called "stents", and more particularly to the stents for blood vessels.

Over the years, the implantation of luminal endoprostheses has become an approved technique for treatment of aneurysms, atherosclerosis, etc.

However, one crucial problem has still not been solved: namely that of perfectly matching the mechanical characteristics of these endoprostheses and of the organs in which they are implanted.

Even if very particular care has been taken to meet these criteria at the time of implantation, a disparity invariably develops in the long term. This is because the human body is subject to changes due to aging, while the endoprosthesis has a problem of stability over the course of time: tearing of the filaments, deterioration of the structure, possible increase in diameter (by loosening of the structure).

The mechanical characteristics of a stent are determined essentially by the structure of its framework. Although different types of these exist, such as the frameworks made up of flat braids described in WO 99/55256, the most suitable framework at present is the cylindrical braided framework, such as is described in particular by Didcott in GB-1205743, or in U.S. Pat. No. 5,061,275.

This type of framework compresses easily for insertion, resists well to crushing and retains a relative flexibility compatible with that of the blood vessels; the structure adapts to the sinuous course of the rigid arteries to be treated.

To date, investigations into finding the optimum framework have focused on the choice of material, the braiding pitch, etc.

These investigations inevitably come up against a number of practical problems.

By adopting a very small braiding pitch (the angle between the axis and the spirals being close to 90°) or by choosing thick wires, the radial force (resistance to crushing) is increased, but flexibility is lost. This problem is even more critical for stents and endoprostheses made up of several modules cut by laser.

Conversely, a large pitch, where the angle formed between the axis and the spirals is close to 30° for example, and the use of thin wires give the framework good flexibility but a low resistance to crushing. In addition, such a pitch signifies a considerable rate of shortening at the time of implantation of the endoprosthesis, which entails a lack of precision upon deployment.

Attempts have been made, particularly in EP-0 804 909, to combine metal wires with textile fibres. This technique is aimed exclusively at the treatment of aneurysms and cannot be applied, for example, to treatment of stenosis of the carotid or even femoral artery. However, the results obtained are not convincing: the metal filaments deform the structure and, along their helical course, they create dislocations and spacing of the textile fibres. The fibres are subjected to stresses under the effect of the pulsations caused by the blood flow and they are subject to rapid erosion by friction against the metal filaments (whose modulus of elasticity and diameter are greater).

Results based on recent clinical studies have shown that, in the case of an aneurysm of the abdominal aorta, 70% of the pressure wave is transmitted to the wall of the aneurysm via the endoprosthesis. (Reference: *Communication at the 27th Global Vascular Endovascular Issues Techniques Horizons™* Nov. 16-19, 2000, page V5.1). These findings are not surprising because haemodynamics teach us that when the walls are thin, the work necessitated by the transport of the blood increases. It is also known that when the vessels are too large, the volume of blood increases beyond what is necessary. These factors promote aneurysms. This shows that more stable and more robust structures have to be developed. This is the object of the invention described below.

SUMMARY OF THE INVENTION

The invention concerns a stent equipped with a braided framework, wherein the framework comprises a plurality of interconnected layers, each of these layers being formed by two plies of metal wires, which are respectively dextrogyratory and laevogyratory and which are interlaced and form a lattice, a plurality of metal wires of a given layer being integrated in the lattice of at least one of the adjacent layers, this plurality of layers providing the side wall of this stent with a porosity transforming a haemodynamic convection flow through this wall into a diffusion flow.

The multilayer stent has advantages over the other single-layer, braided stents. It has the benefit of increased radial strength, a stability over a longer period of time, and better adaptation, due to the number of layers, to the type of artery and its pathology.

The structure uses a single type of material, ensuring its robustness and homogeneity.

The structure also affords the possibility of attaching a cover made of PTFE or Dacron.

In the case of a metal framework, the wires are preferably chosen from among the following materials [Phynox®, Elgiloy®, titanium and its alloys, Nitinol]. After the braiding stage, the metal wires of the stent according to the invention can undergo heat treatment to impart a phase transition (giving them the required structural stability and rigidity), in contrast to the hybrid stents of EP 0 804 909 A2 cited above.

It is in fact commonly acknowledged that any wire which has been hardened by heat treatment loses its elasticity and its plastic deformation and that consequently it becomes rigid. It is thus strongly inadvisable to re-work a wire hardened by heat treatment, as is the case in a hybrid stent: the heat treatment is impossible to apply a posteriori, in the presence of textile fibres which would melt or burn. According to an advantageous embodiment, the framework comprises wires of different thicknesses.

The thickness of the wires can lie within the range of between 25 and 60 microns.

The advantage of using thin wires with a size of the interstices (comparable to the pores of a filtering structure), arranged in multilayers, adjusted to a dimension of between 100 and 200 μm, is that they do not greatly disturb the blood flow: it is therefore possible to use them for endoprostheses without cover layers (stents) which ensure that particles originating from the vessels do not ascend towards the brain and cause thrombosis or even strokes.

The advantage of using thicker wires is that they afford a better hold against the wall of the vessels and allow the endoprosthesis to withstand, without damage, the various stresses to which the vessels are subjected, especially in the areas of the neck and the knee.

The use of interconnected layers also solves the thorny issue of correlating three critical problems not solved by the prior art: using sheets of wires with materials having different mechanical characteristics or structures made from assembled modules, it is found that the endoprostheses of the prior art (principally those intended for aneurysms) have a tendency to migrate longitudinally, to change shape over time, and to degrade.

Conversely, in a prosthesis according to the invention, the mechanical properties of the wires of the different plies can be balanced in such a way as to perfectly compensate each other and ensure long-term stability.

BRIEF DESCRIPTION OF THE DRAWINGS

Other features and advantages of the invention will become evident from the following description of particular embodiments of the invention, with reference being made to the attached drawings in which.

DETAILED DESCRIPTION OF THE DRAWINGS

Figure 1:
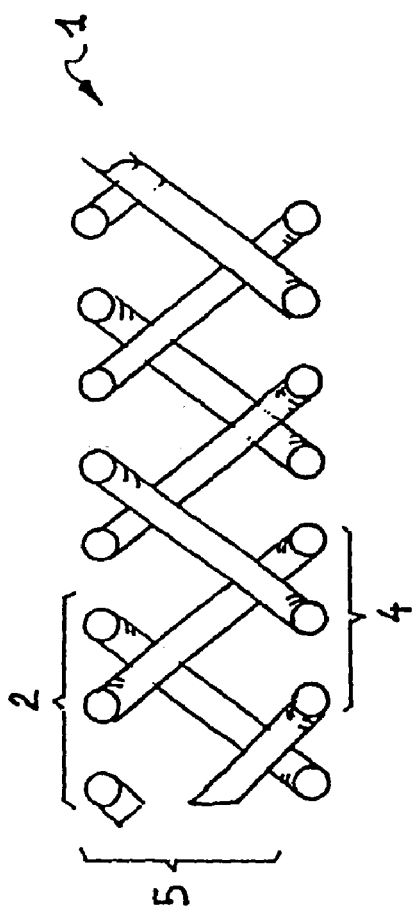
FIG. 1 is a side view of a traditional braided stent framework.
Figure 2:
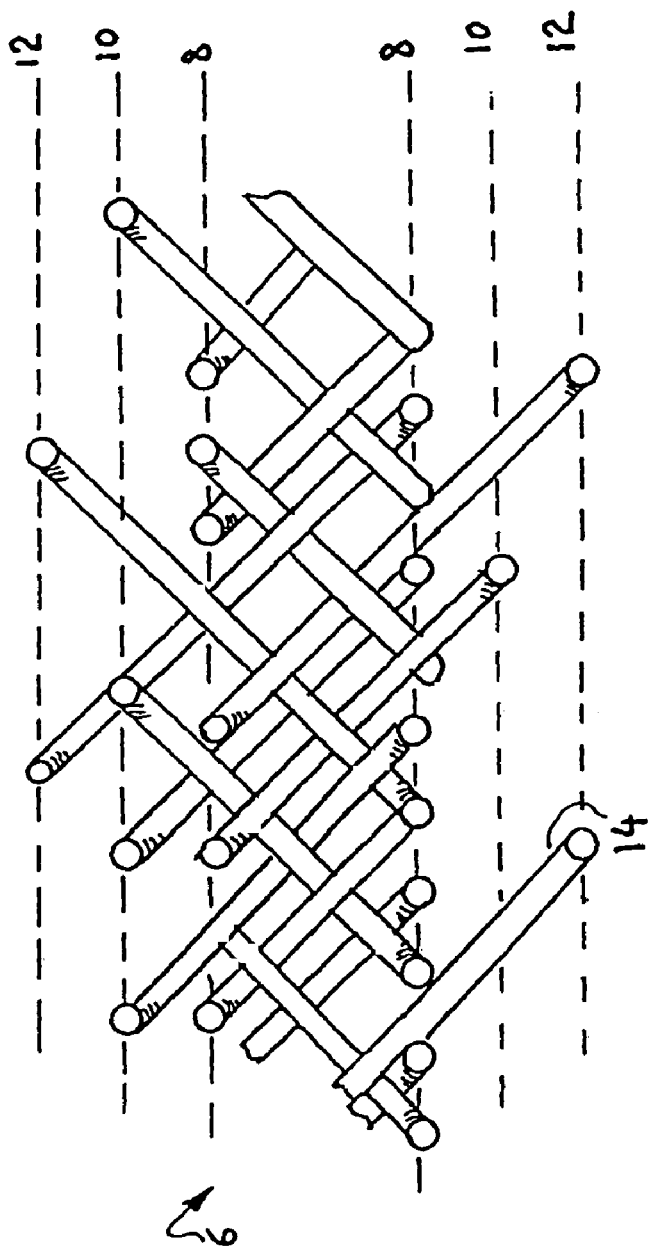
FIG. 2 is a simplified diagrammatic view of the stent framework according to the invention.

The traditional braided framework 1 is made up of a simple braid, two plies 2, 4 of wires, which are dextrogyratory 2 and laevogyratory 4, respectively, intersecting to form a simple braid 5.

The framework 6 of the invention is a multiple braid which comprises, in the example shown, three layers 8, 10, 12 whose plies are not distinct: at the time of braiding, a given number of wires 14 of the plies of the first layer 8 are interlaced with the plies of the second layer 10 and/or of the third layer 12, forming a complex lattice (this applies to the figure shown, but it goes without saying that the interlacing can continue to the Nth layer if the number of layers is N). This manner of proceeding opens up enormous possibilities for adjusting the characteristics of the framework. Not only does it permit a wide variety of "standards" depending on the organs involved, it also in practice permits adjustment case by case by acting on the pitch of the braid, the diameter and the nature of the wires 14, the density of the braiding, the number of layers 8, 10, 12, the number of wires 14 of different diameters, and the interlacing of the layers.

It would of course be pointless citing all these advantages if the endoprostheses equipped with such a framework could not be implanted using existing equipment.

However, one of the unexpected aspects of the invention is that, despite the large number of wires 14 used, the thickness of the successive layers 8, 10, 12 and the complexity of the structure, the exclusively metal multiple braid can be very easily reduced to a diameter comparable to that of a traditional framework 1. Unlike the wires or strands of the composite multi-layer frameworks or even single-layer frameworks, those of the present multilayer framework tend to occupy the space in a more effective way, probably by virtue of the complex interpenetration of the layers.

It is therefore easily possible to use a conventional introducing instrument to implant a stent equipped with the novel structure, even in vessels of small diameter.

Moreover, the stent according to the invention can, after deployment, assume very large diameters (especially for an aortic dissection or in the case of the oesophagus) without risk of crushing.

The present structure also allows the layers 8, 10, 12 formed of wires 14 of different diameters to act in synergy. Clinical trials conducted by practitioners (surgeons, radiologists and cardiologists) in which two stents 1 of different characteristics have simply been introduced one within the other have had mixed results or have failed, whereas the present structure 6 significantly increases the resistance to crushing without reducing flexibility.

This characteristic is important particularly in the treatment of aneurysms. This is because, over the course of time, an aneurysm tends to shorten in the longitudinal direction. A classical stent placed in these circumstances will tend to undulate and finally crush, which is not the case with the present structure.

Moreover, as has been mentioned above, the multilayer structure 6 permits the use of wires of very fine diameter which can act as a filtering structure in combination with thicker strengthening wires.

The interlacing of these wires provides for a regular spatial distribution, ensuring a regular meshwork favourable to uniform filtering of the particles.

In addition to their inherent mechanical characteristics, it is also possible to make advantageous use of the particular features imposed on the wires by appropriate technical treatment.

It is thus possible to take advantage of the use of Nitinol wires, such as are described in the application PCT/BE98/00076, to achieve reinforcement of the structure after it has been implanted.

Figure 3:
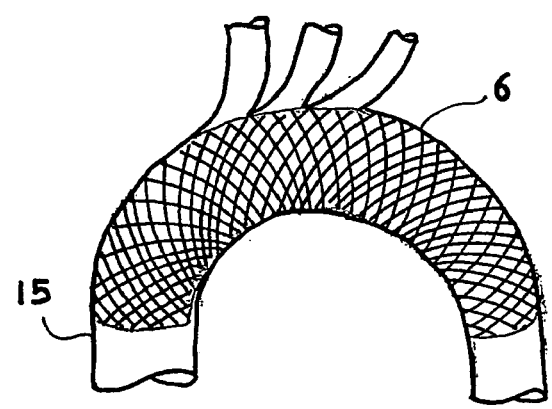
FIG. 3 is a diagrammatic view showing the use of a stent according to the invention in a carotid artery.

FIG. 3 shows that, in addition to acting as a classical stent, the stent according to the invention can be successfully positioned at a site thought dangerous, for example the carotid bifurcation. However, the framework according to the invention makes it possible to manufacture stents which go from 6 to 50 mm in diameter; it is therefore safer and easier to place the stent—diameter preferably 25 to 40 mm—in the aortic arch 15 opposite the subclavian and vertebral arteries. It is thus possible to avoid the problem of embolisms upstream of the carotid artery more easily in terms of deployment, and more appropriately in terms of safety.

The use of the multilayer structure and of metal wires whose diameter is between 25 μm and 60 μm permits realization of a structure which is both stable and effective.

Figure 4:
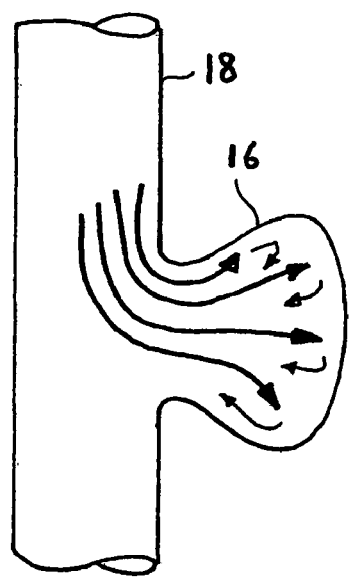
FIGS. 4 and 5 show the reduction of an aneurysm with the stent according to the invention.
Figure 5:
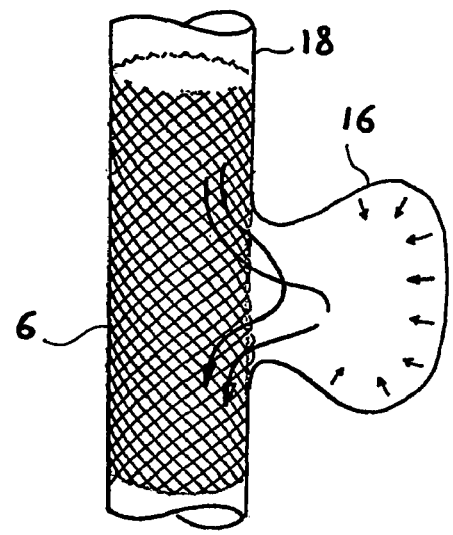

FIGS. 4 and 5 illustrate the possibility of using the stent according to the invention to solve, in a hitherto unconventional way, the problem caused by aneurysms.

The classical approach to reducing aneurysms 16 has hitherto involved fitting the affected vessel 18 with an endoprosthesis equipped with a leaktight polymer covering. The practically inevitable deformation of this endoprosthesis, however, leads to the gradual appearance of leaks between this endoprosthesis and the wall of the vessel 18, especially in the case of fusiform aneurysms 16. The pouch formed by the aneurysm 16 is thus subjected to the same stresses as before and ceases to resorb. It is however possible to treat aneurysms without using so-called leaktight covers. Studies (Annals of Biomedical Engineering, Vol. 25, pages 460-469; 1997) show that by implanting a stent whose walls are within a very precise range of porosity, it is in theory possible to alter the haemodynamics in an aneurysm by transforming the convection flow (as shown in FIG. 4) to a diffusion flow (see FIG. 5), which reduces the pressure in the pouch 16, so that the latter is able to resorb normally. By adjusting the number of wires, the number of layers and the size of the gaps between the wires, it is possible to obtain the required porosity with the present stent, thus opening up a practical possibility of applying the technique described above.

The invention claimed is:

1. Luminal endoprosthesis consisting of a braided framework which includes a plurality of layers of biocompatible metal wires which are interlaced, each of these layers being formed by two plies of wires, which are respectively dextrogyratory and laevogyratory, and which are interlaced and form a lattice, a plurality of wires of a given layer being integrated in the lattice of at least one of the adjacent layers, wherein the metal of the wires is devoid of crystalline dislocation, the plurality of layers providing the side wall of the endoprosthesis with a porosity transforming a haemodynamic convection flow through the wall into a diffusion flow.

2. Luminal endoprosthesis according to claim 1, wherein the material of the wires is selected from the group consisting of stainless steel, cobalt-chromium-nickel alloys, titanium and its alloys, and Nitinol.

3. Luminal endoprosthesis according to claim 1, wherein the framework comprises metal wires of different thicknesses.

4. Luminal endoprosthesis according to claim 2, wherein the framework comprises metal wires of different thicknesses.

5. Luminal endoprosthesis according to claim 4, wherein the framework comprises layers formed by wires of different thickness.

6. Luminal endoprosthesis according to claim 5, wherein the thickness of the wires lies at least within a range of between 25 and 60 microns.

7. Luminal endoprosthesis according to claim 4, wherein the framework comprises wires made of different types of metals.

8. Luminal endoprosthesis according to claim 3, wherein the framework comprises layers formed by wires of different thickness.

9. Luminal endoprosthesis according to claim 8, wherein the thickness of the wires lies at least within a range of between 25 and 60 microns.

10. Luminal endoprosthesis according to claim 3, wherein the framework comprises wires made of different types of metals.

* * * * *

UNITED STATES PATENT AND TRADEMARK OFFICE
CERTIFICATE OF CORRECTION

PATENT NO. : 7,588,597 B2 Page 1 of 1
APPLICATION NO. : 10/450315
DATED : September 15, 2009
INVENTOR(S) : Noureddine Frid It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 571 days.

Signed and Sealed this

Twenty-first Day of September, 2010

David J. Kappos
*Director of the United States Patent and Trademark Office*